US010564432B2

(12) United States Patent
Inoue et al.

(10) Patent No.: US 10,564,432 B2
(45) Date of Patent: Feb. 18, 2020

(54) HEAD-MOUNTED DISPLAY UNIT AND HEAD-MOUNTED DISPLAY FIXING STAND

(71) Applicant: CREWT MEDICAL SYSTEMS, INC., Tokyo (JP)

(72) Inventors: Satoshi Inoue, Tokyo (JP); Hiroki Sato, Tokyo (JP); Kenzo Yamanaka, Tokyo (JP); Shinji Kimura, Tokyo (JP)

(73) Assignee: CREWT MEDICAL SYSTEMS, INC., Tokyo (JP)

( * ) Notice: Subject to any disclaimer, the term of this patent is extended or adjusted under 35 U.S.C. 154(b) by 0 days.

(21) Appl. No.: 15/765,296

(22) PCT Filed: Oct. 3, 2016

(86) PCT No.: PCT/JP2016/079239
§ 371 (c)(1),
(2) Date: Apr. 2, 2018

(87) PCT Pub. No.: WO2017/057771
PCT Pub. Date: Apr. 6, 2017

(65) Prior Publication Data
US 2018/0252927 A1  Sep. 6, 2018

(30) Foreign Application Priority Data
Oct. 2, 2015 (JP) ................................. 2015-196690

(51) Int. Cl.
*G02B 27/01* (2006.01)
*A61B 3/00* (2006.01)
(Continued)

(52) U.S. Cl.
CPC ........ *G02B 27/0176* (2013.01); *A61B 3/0083* (2013.01); *G02B 27/0172* (2013.01); *G02B 27/028* (2013.01); *A61B 3/024* (2013.01)

(58) Field of Classification Search
CPC ........... A61B 3/00; A61B 3/10; A61B 3/1015; A61B 3/032; A61B 3/113; A61B 5/162;
(Continued)

(56) References Cited

U.S. PATENT DOCUMENTS

| 6,045,227 A * | 4/2000 | Stewart | A61B 3/032 351/237 |
| 6,612,700 B2 * | 9/2003 | Walther | A61B 3/0075 351/224 |

(Continued)

FOREIGN PATENT DOCUMENTS

| JP | H08-131399 A | 5/1996 | |
| JP | H08-196514 A * | 8/1996 | .............. A61B 1/04 |

(Continued)

OTHER PUBLICATIONS

Dec. 27, 2016 International Search Report issued in International Patent Application No. PCT/JP2016/079239.

*Primary Examiner* — Richard J Hong
(74) *Attorney, Agent, or Firm* — Oliff PLC

(57) ABSTRACT

Physical burden when a head-mounted display is mounted to the head of a user for use is reduced. A head-mounted display unit includes a head-mounted display, and a fixing stand configured so as to enable the attachment and detachment of the head-mounted display, and to enable the head-mounted display to be mounted in a fixed state. The fixing stand includes a base member, a support column projecting perpendicularly upwards from the base member, a pedestal mount attached to an upper end portion of the support column, a retaining member attached to the pedestal mount, a clamping implement, and a chin rest. The fixing stand is configured such that the head-mounted display is detachably mounted to the retaining member using the clamping implement.

14 Claims, 14 Drawing Sheets

(51) Int. Cl.
*G02B 27/02* (2006.01)
*A61B 3/024* (2006.01)

(58) Field of Classification Search
CPC ..... A61B 3/0075; A61B 3/112; A61B 3/0025; A61B 3/0083; A61B 3/024; G02B 27/0172; G02B 27/0176; G02B 27/028; G02B 27/017; F16M 11/10
See application file for complete search history.

(56) References Cited

U.S. PATENT DOCUMENTS

| | | | | |
|---|---|---|---|---|
| 2005/0099601 | A1* | 5/2005 | MacDougall | A61B 3/113 351/209 |
| 2005/0174535 | A1* | 8/2005 | Lai | A61B 3/1015 351/205 |
| 2007/0188407 | A1* | 8/2007 | Nishi | F16M 11/10 345/8 |
| 2007/0236663 | A1* | 10/2007 | Waldorf | A61B 3/112 351/206 |
| 2009/0228124 | A1* | 9/2009 | Kato | G02B 27/017 700/94 |
| 2014/0154650 | A1* | 6/2014 | Stack | A61B 5/162 434/236 |
| 2015/0131055 | A1* | 5/2015 | Catanzariti | A61B 3/0025 351/212 |

FOREIGN PATENT DOCUMENTS

| | | |
|---|---|---|
| JP | 2002-236957 A | 8/2002 |
| JP | 2014-100254 A | 6/2014 |

\* cited by examiner

HEAD-MOUNTED DISPLAY UNIT AND HEAD-MOUNTED DISPLAY FIXING STAND

TECHNICAL FIELD

The present invention relates to a head-mounted display unit and to a head-mounted display fixing stand.

DESCRIPTION OF RELATED ART

Known image display devices include head-mounted displays (HMDs) that are mounted to the head of a user for use. Head-mounted displays are mainly proffered for applications such as gaming machines and audio visual (AV) devices.

On the other hand, technology in which head-mounted displays are employed as medical devices is also known. Specifically, head-mounted type eye testing device is known in which a head-mounted display is employed to perform eye testing (see, for example, Patent Document 1). With such an eye testing device, an eye test is performed by mounting a head-mounted display on the head of a testee and displaying visual target for testing on the eyeball of the testee while in this mounted state.

PRIOR ART DOCUMENT

Patent Document

Patent Document 1: Japanese Patent Laid Open Publication No. 2014-100254.

SUMMARY OF INVENTION

Technical Problem

However, the head-mounted type eye testing device tends to be heavier than head-mounted displays for applications such as gaming machines. Thus, considerable weight of the head-mounted display is added on the neck and shoulders of the testee when the head-mounted display is mounted to the head of the testee for use. A heavy physical burden is felt from the weight of the head-mounted display, particularly when the testee is an elderly person or a child.

A main object of the present invention is to provide technology to enable physical burden to be reduced when a head-mounted display is mounted for use on the head of a user.

Solution to Problem (First Aspect)

A first aspect of the present invention is a head-mounted display unit including a head-mounted display and a fixing stand configured so as to enable attachment and detachment of the head-mounted display, and so as to enable the head-mounted display to be mounted in a fixed state.

(Second Aspect)

A second aspect of the present invention is the head-mounted display unit of the first aspect, wherein the fixing stand supports the head-mounted display in a forward-tilting orientation.

(Third Aspect)

A third aspect of the present invention is the head-mounted display unit of the first or second aspect, wherein the fixing stand is portable.

(Fourth Aspect)

A fourth aspect of the present invention is the head-mounted display unit of any one of the first to the third aspects, wherein the head-mounted display is a head-mounted type eye testing device.

(Fifth Aspect)

A fifth aspect of the present invention is a head-mounted display fixing stand for fixing a head-mounted display for use, including a retaining member configured so as to enable the detachable mounting of the head-mounted display and so as to retain the mounted head-mounted display in a fixed state, and a support mechanism to support the retaining member.

(Sixth Aspect)

A sixth aspect of the present invention is the head-mounted display fixing stand of the fifth aspect, wherein a front-rear tilting angle of the head-mounted display is adjustable.

(Seventh Aspect)

A seventh aspect of the present invention is the head-mounted display fixing stand of the fifth or sixth aspect, further including a chin rest to support a chin of a user using the head-mounted display.

(Eighth Aspect)

An eighth aspect of the present invention is the head-mounted display fixing stand of the seventh aspect wherein a position of the chin rest is adjustable.

(Ninth Aspect)

A ninth aspect of the present invention is the head-mounted display fixing stand of any one of the fifth to eighth aspects, further including a monitor to display images to someone other than a user using the head-mounted display.

(Tenth Aspect)

A tenth aspect of the present invention is the head-mounted display fixing stand of the ninth aspect, wherein the monitor is disposed in a state in which a display area of the monitor is orientated in front of or at a side of the retaining member.

(Eleventh Aspect)

An eleventh aspect of the present invention is the head-mounted display fixing stand of the ninth or tenth aspect, wherein the orientation of the monitor is adjustable.

(Twelfth Aspect)

A twelfth aspect of the present invention is the head-mounted display fixing stand of any one of the fifth to eleventh aspects, further including a handle including a left and right pair of grips.

(Thirteenth Aspect)

A thirteenth aspect of the present invention is the head-mounted display fixing stand of any one of the fifth to twelfth aspects, wherein the retaining member includes a second terminal section corresponding to a first terminal section provided to the head-mounted display, and the first terminal section and the second terminal section are electrically connected when the head-mounted display is mounted to the retaining member.

(Fourteenth Aspect)

A fourteenth aspect of the present invention is the head-mounted display fixing stand of the thirteenth aspect, wherein the first terminal section and the second terminal section are terminal sections for charging a rechargeable battery installed in the head-mounted display.

Advantageous Effects

The present invention enables physical burden to be reduced when a head-mounted display is mounted to a head of a user for use.

BRIEF DESCRIPTION OF DRAWINGS

FIG. 13 illustrates a configuration of a head-mounted display unit according to another embodiment of the present invention.

DESCRIPTION OF EMBODIMENTS

Embodiments of the present invention will be described in detail, with reference to the drawings.

In this embodiment of the present invention, explanation will be given in the following sequence.

1. Overall Configuration of Head-Mounted Display Unit.
2. Configuration of Head-Mounted Display
3. Configuration of Optical System of Head-Mounted Display
4. Configuration of Fixing stand
5. Usage Procedure of Head-Mounted Display Unit
6. Advantageous Effects of Embodiment
7. Other Embodiments.
8. Modified Examples etc.

1. Overall Configuration of Head-Mounted Display Unit

Figure 1:
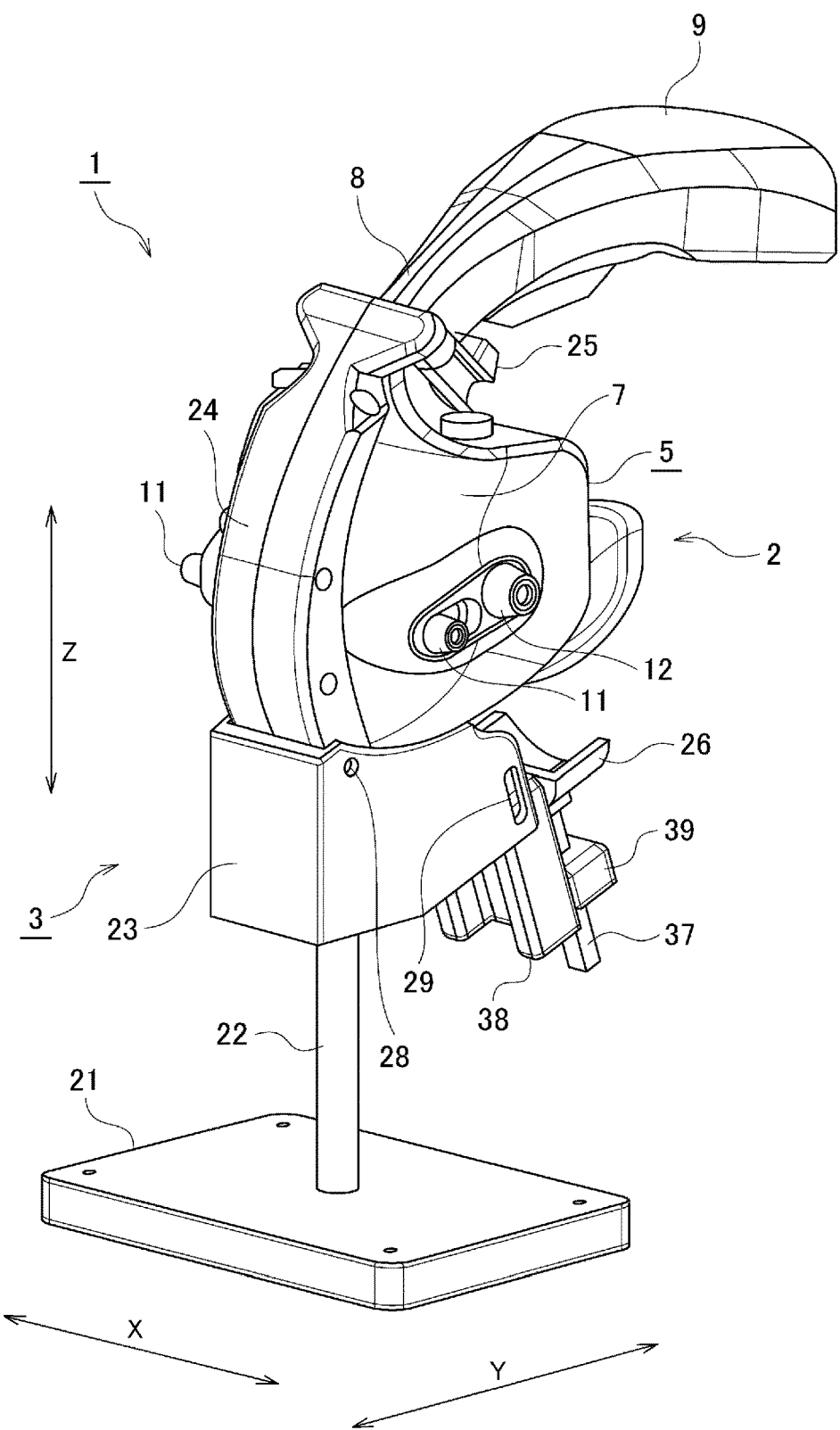
FIG. 1 is a perspective view illustrating an example of a configuration of a head-mounted display unit according to an embodiment of the present invention.
Figure 2:
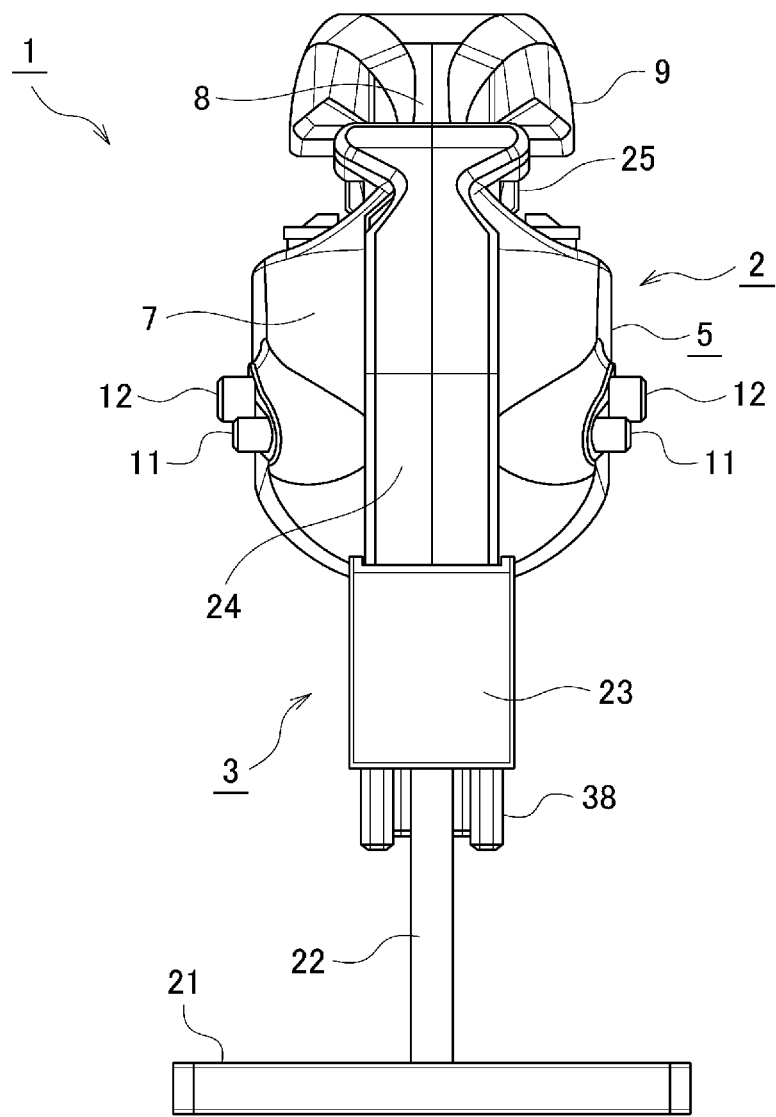
FIG. 2 is a front view illustrating an example of a configuration of a head-mounted display unit according to an embodiment of the present invention.
Figure 3:
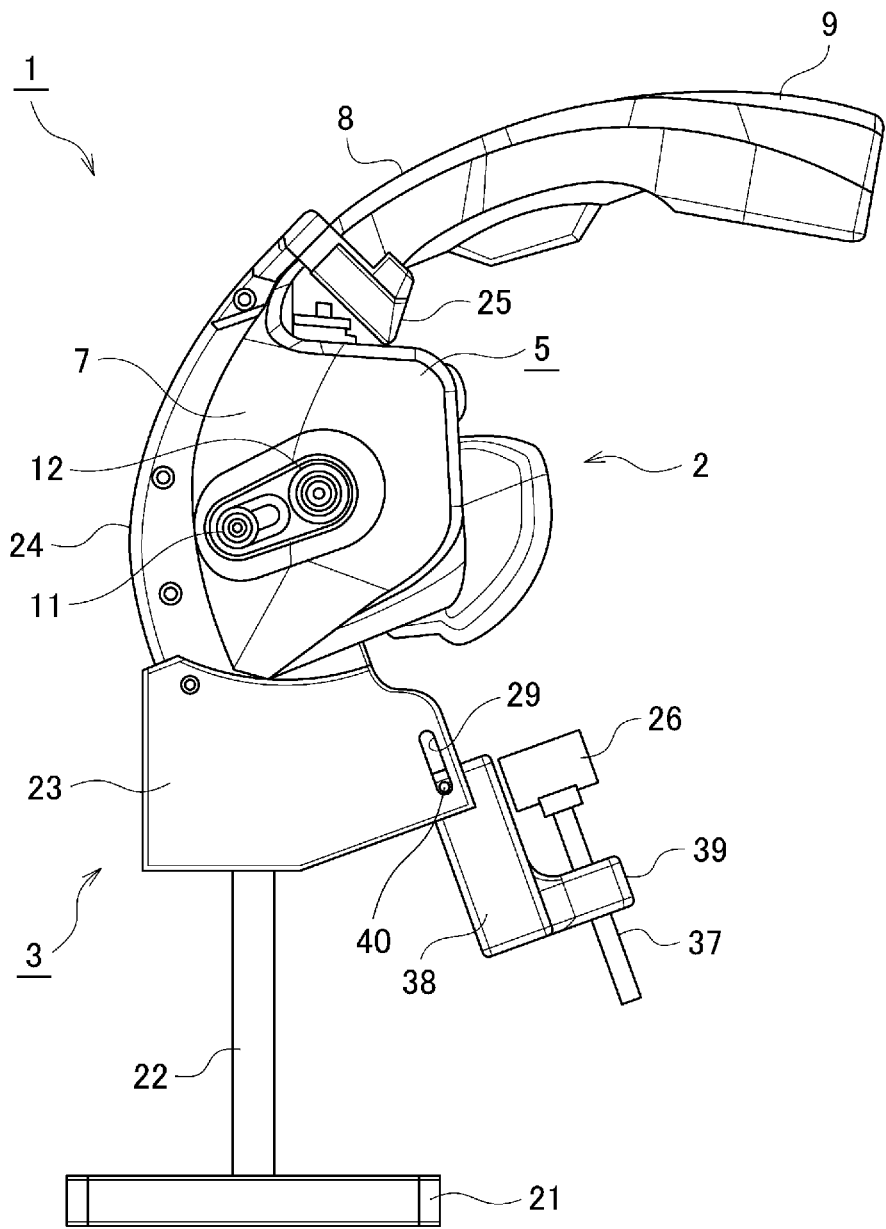
FIG. 3 is a side view illustrating an example of a configuration of a head-mounted display unit according to an embodiment of the present invention.

FIG. 1 is a perspective view illustrating an example of a configuration of a head-mounted display unit according to an embodiment of the present invention; FIG. 2 is a front view of the same, and FIG. 3 is a side view of the same.

The illustrated head-mounted display unit 1 is, broadly speaking, provided with a head-mounted display 2, and a fixing stand 3 for fixing the head-mounted display 2.

The head-mounted display 2 is employed when mounted to the head of a user. The head-mounted display 2 is able to be used in various applications, and is equipped with appropriate functions according to application. For example, in the present embodiment an example will be explained of a case in which the head-mounted display 2 is a head-mounted type eye testing device. Among eye testing devices there are, for example, visual field testing devices, visual acuity testing devices, ocular muscle function testing devices, and the like. The present invention is applicable to all such eye testing devices; however, in this embodiment an example will be explained of application of the present invention to a visual field testing device from among the above.

The fixing stand 3 is an apparatus (head-mounted display fixing stand) employed to fix the head-mounted display 2. Namely, the fixing stand 3 fixes an originally mobile type head-mounted display 2 to a predetermined location, so as to thereby enable the use thereof as a fixed type.

A configuration of the head-mounted display 2 and a configuration of the fixing stand 3 will now be explained in sequence. Note that in the following explanation, as illustrated in FIG. 1, a direction X is a left-right direction, a direction Y is a front-rear direction, and a direction Z is an up-down direction from the perspective of a user when using the head-mounted display 2 fixed using the fixing stand 3 by mounting to the head of the user.

2. Configuration of Head-Mounted Display

Figure 4:
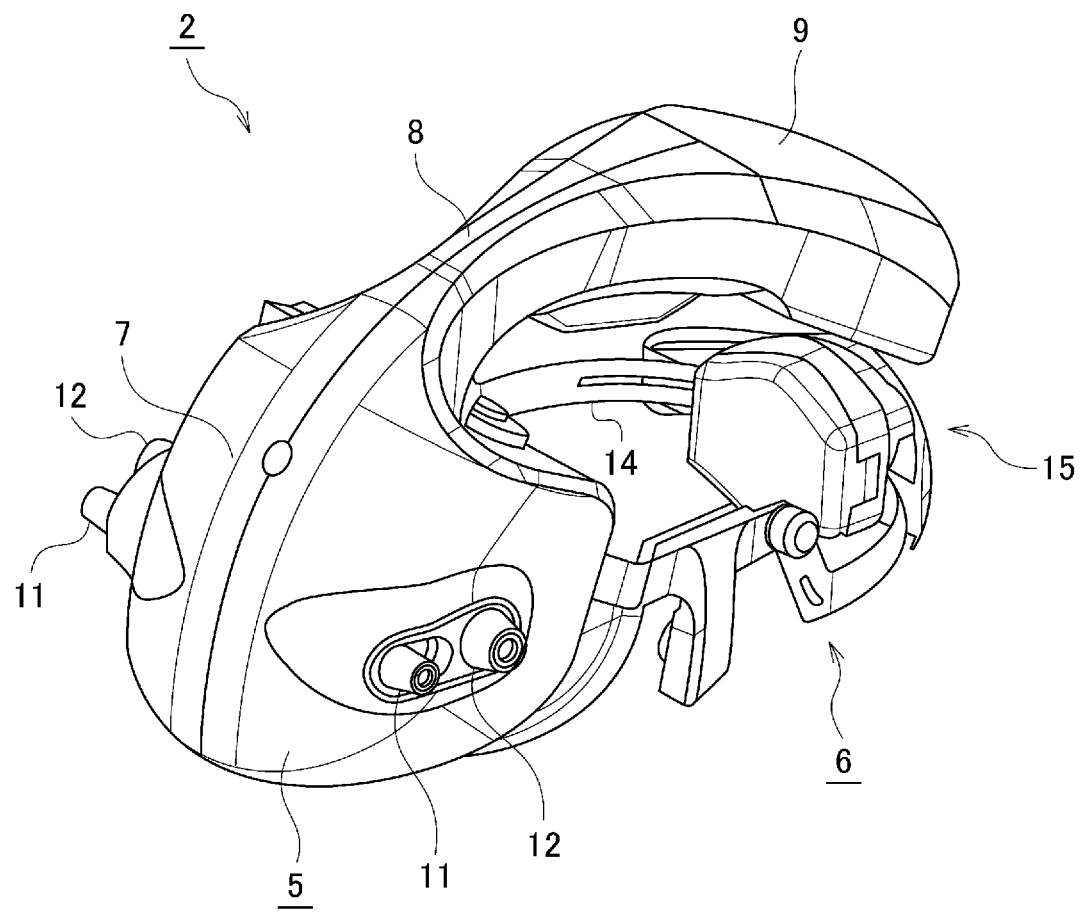
FIG. 4 is a perspective view illustrating an example of a configuration of a head-mounted display according to an embodiment of the present invention.

FIG. 4 is a perspective view illustrating an example of a configuration of a head-mounted display according to an embodiment of the present invention.

The illustrated head-mounted display 2 is provided with a body section 5 installed with an optical system etc., described later, and with a harness 6 to mount the body section 5 on the head of the user. The head-mounted display 2 has a form similar to is a helmet style.

Body Section

The body section 5 is a section actually mounted to the head of a user, and is a single body including a front portion 7, an intermediate portion 8, and a rear portion 9. From out of these portions, the front portion 7 is placed so as to span from in front of the eyes of the user to the front of the head of the user when the body section 5 is mounted to the head of the user. Moreover, the intermediate portion 8 is placed so as to span from the front of the head of the user to the crown of the user, and the rear portion 9 is placed so as to span from the crown of the user to the rear of the head of the user.

An optical system, a display element, and the like for displaying images are installed in the front portion 7. The external surface of the front portion 7 is shaped with a curved face profile so as to follow the shape of the head of the user. A left and right pair of first rotatable knobs 11, and a left and right pair of second rotatable knobs 12, are provided at the two respective sides of the front portion 7. The first rotatable knobs 11 are employed to adjust the central positions of the optical systems (positions of the optical axes) to positions at the center of the pupils of the user. The second rotatable knobs 12 are employed to adjust distances from the positions of the pupils of the user to front lens positions of the optical systems. A left and right pair of observation windows (not illustrated in the drawings) are provided at the inside face of the front portion 7 to enable the user to view images both binocularly and monocularly. A pad (not illustrated in the drawings) against which the forehead of the user can be pressed is further provided at the periphery of these observation windows.

The intermediate portion 8 is formed so as to couple the front portion 7 and the rear portion 9 together. A width of the body section 5 narrows from the left and right directions at a portion from the front portion 7 to the intermediate portion 8, and a width of the body section 5 widens to the left and right directions at a portion from the intermediate portion 8 to the rear portion 9. Thus the intermediate portion 8 is formed with a width narrower than that of the front portion 7 and the rear portion 9. A computer, described later, is installed in the rear portion 9. Moreover, a connection interface (not illustrated in the drawings) is provided on the rear end face of the rear portion 9. The connection interface is employed to connect the computer installed in the rear portion 9 to an external terminal device (not illustrated in the drawings) so as to enable communication therebetween. Moreover, there is a non-illustrated cable that belongs to the head-mounted display 2, and the cable is configured so as to be connectable to the connection interface.

Note that in the present embodiment, the communication between the computer and the terminal device referred to above is anticipated to be performed by wire using the cable; however, the present invention is not limited thereto, and a wireless communication protocol may also be adopted.

(Harness)

The harness 6 is employed to mount the body section 5 to the head of the user stably when the head-mounted display 2 is employed as a mobile type head-mounted display 2. The harness 6 is configured so as to be attachable to the body section 5 and detachable from the body section 5. The harness 6 includes a belt 14 capable of being wrapped around the head of the user, and an adjuster 15 enabling the length of the belt 14 to be adjusted. The belt 14 is formed in a substantially letter U-shape so as to wrap from the side of the head of the user, around to the rear of the head of the user. The adjuster 15 is employed to achieve an appropriate fastening force on the head of the user, or to release such fastening force, by adjusting the length of the belt 14 to match the head circumference (the length of the head circumference) of the user.

3. Configuration of Head-Mounted Display Optical System

Figure 5:
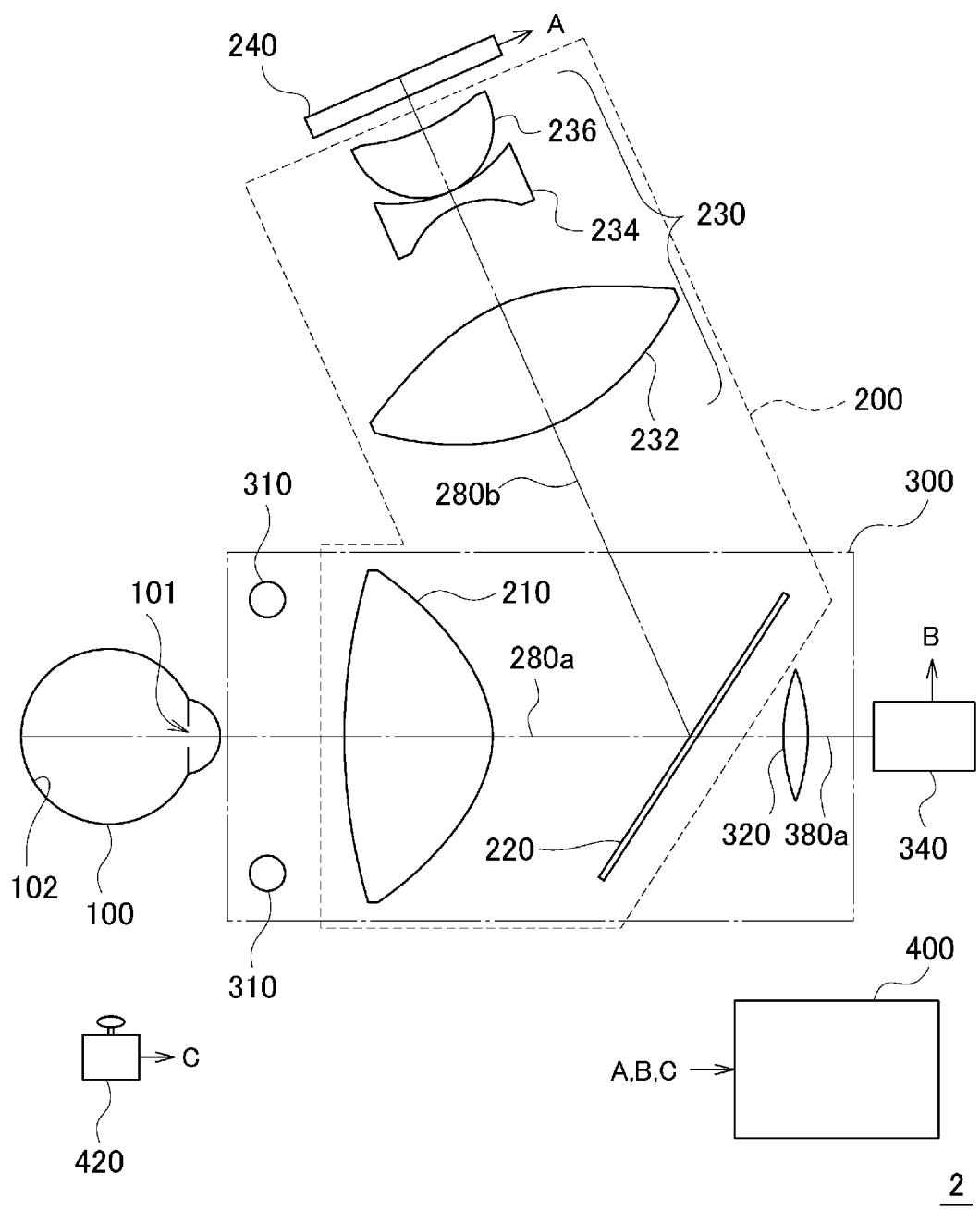
FIG. 5 is a schematic diagram containing a configuration of optical systems of a head-mounted display according to an embodiment of the present invention.

FIG. 5 is a schematic diagram including a configuration of optical systems of a head-mounted display according to an embodiment of the present invention.

As illustrated, the head-mounted display 2 includes a display optical system 200, a display element 240, an observation optical system 300, an imaging element 340, a controller 400, and a testee operated section 420. In the present embodiment, the head-mounted display 2 is employed as a visual field testing device. In such cases, the user of the head-mounted display 2 is a testee receiving a visual field test. The display optical system 200 and the display element 240 are configuration elements for displaying test images to the testee. The observation optical system 300 and the imaging element 340 are configuration elements for observing the respective eyeballs 100 of the testee. The display element 240, the testee operated section 420, and the imaging element 340 are each electrically connected to the controller 400, as indicated by the reference signs A, B, C in the drawing. Note that although in FIG. 5 the configuration elements (200, 240, 300, 340) corresponding to one eye of the testee are illustrated, there are in fact configuration elements as described above corresponding to the two eyes of the testee independently provided on the left and right.

In the present embodiment, a visual target is included in test images for display on the display element 240, so as to present the visual target to the testee. A visual target refers to a "point" or "figure" displayed (presented) with light on the eyeball of the testee to impart stimulation.

(Display Optical System)

The display optical system 200 is provided on the optical axes 280a, 280b between the eyeball positions where the eyeballs 100 of the testee are disposed and the display area of the display element 240. Specifically, the display optical system 200 is configured by a first lens 210, a mirror 220, and a second lens group 230 disposed in this sequence from the side of the testee's eyeball position. Explanation follows regarding each of the configuration elements. Note that in the following explanation, from out of the optical axes 280a, 280b that run from the testee's eyeball position to the display element 240, the optical axis from the eyeball position to the mirror 220 is the optical axis 280a, and the optical axis from the mirror 220 to the display element 240 is the optical axis 280b.

The first lens 210 is disposed on the optical axis 280a that runs from the eyeball position to the mirror 220. The first lens 210 is configured by a lens (convex lens) having a positive power and aspherical surfaces. The first lens 210 is employed on the one hand to converge light reflected at the mirror 220 and incident to the first lens 210 so as to converge at a pupil 101 of the testee, and also to suppress divergence of light when the testee looks at an object over a wide angle through the pupil 101.

The mirror 220 is disposed on the optical axis 280a that runs from the eyeball position to the mirror 220, on the opposite side of the first lens 210 to the eyeball position. The mirror 220 is configured by a mirror having wavelength selectivity. Specifically, the mirror 220 is configured by a cold mirror that reflects visible light and transmits infrared light.

The second lens group 230 is disposed on the optical axis 280b that runs from the mirror 220 to the display element 240. The second lens group 230 is configured by three lenses 232, 234, 236. The three lenses 232, 234, 236 are disposed in this sequence from the mirror 220 side to the display element 240 side.

The lens 232 is configured by a lens (convex lens) having a positive power and aspherical surfaces. Moreover, the lens 234 is configured by a lens (convex lens) having a negative power and aspherical surfaces, and the lens 236 is configured by a lens (convex lens) having a positive power and aspherical surfaces.

(Display Element)

The display element 240 is disposed on the optical axis 280b that runs from the mirror 220 to the display element 240, so as to face toward the lens 236 of the second lens group 230. The display element 240 is configured, for example, by a flat screen type display element, such as a liquid crystal display element including a backlight.

(Observation Optical System)

The observation optical system 300 is employed to observe the testee's eyeball 100 as an observation target and, for example, observes the anterior eye including the pupil 101, the iris, and the sclera, the fundus including a retina 102, or the like. The configuration elements of the observation optical system 300 are, apart from infrared light sources 310, provided on the optical axes 280a, 380a that run from the testee's eyeball position to the imaging element 340. Specifically, a configuration is adopted in which the first lens 210, the mirror 220, and a third lens 320 are disposed in this sequence from the testee's eyeball position side. Of these configuration elements, the first lens 210 and the mirror 220 are included on the optical axis 280a and are common to (commonly employed with) the display optical system 200 described above. Moreover, the optical axis 380a that runs from the mirror 220 to the imaging element 340 is substantially parallel to the optical axis 280a.

The infrared light sources 310 irradiate infrared light onto the testee's eyeball 100. The infrared light sources 310 are disposed apart, diagonally above and diagonally below the testee's eyeball position so as not to interfere with the field of view of the testee. In this configuration, one of the infrared light sources 310 irradiates infrared light onto the testee's eyeball 100 from diagonally above, and the other of the infrared light sources 310 irradiates infrared light onto the testee's eyeball 100 from diagonally below.

The third lens 320 is disposed on the optical axis 380a that runs from the mirror 220 to the imaging element 340. The third lens 320 is configured by a lens (convex lens) having a positive power and aspherical surfaces. When the first lens 210 is used as an object lens to observe the eyeball 100, the third lens 320 forms an image at the imaging plane of the imaging element 340 with light from the eyeball 100 incident to the first lens 210 and passing through the mirror 220.

(Imaging Element)

The imaging element 340 images the testee's eyeball 100 through the observation optical system 300 described above. The imaging element 340 is configured by a charge coupled device (CCD) imaging element, a complementary metal oxide semiconductor (CMOS) imaging element, or the like having sensitivity to infrared light.

In the observation optical system 300 and imaging element 340 configured as described above, while infrared radiation from the infrared light sources 310 is being irradiated onto the testee's eyeball 100, an image of the eyeball 100 is imaged by the imaging element 340 through the first lens 210, the mirror 220, and the third lens 320.

The controller 400 is configured by a computer that combines a central processing unit (CPU), random access memory (RAM), read only memory (ROM), a hard disk drive (HDD), various interfaces, and the like. The controller 400 is configured so as to implement various functions by the CPU executing a predetermined program stored on the ROM or HDD. The predetermined program to implement various functions is used by installing on the computer; however, before being installed, the predetermined program may be provided stored on a computer readable storage medium before being installed, or may be provided through a communication line connected to a computer.

The testee operated section 420 is operated by the testee. The testee operated section 420 is mainly operated by the testee to make responses. The testee operated section 420 is preferably a manual testee operated section that is hand held and operated by the testee, and is more preferably a press-style testee operated section operated by press operation by a finger (for example, the thumb or index finger) on a hand of the testee. In such cases, when the testee press-operates the testee operated section 420, the testee operated section 420 switches between an OFF state and an ON state, and an ON signal is output from the testee operated section 420. This ON signal is acquired by the controller 400.

Using the head-mounted display 2 configured as described above enables kinetic perimetry (Goldmann perimetry), static perimetry, fundus perimetry (micro perimetry), electroretinography (ERG), or other test to be performed. As an example thereof, explanation follows regarding a case in which static perimetry is performed.

The static perimetry is performed in the following manner. First, a visual target is presented at a single point within the field of view, and the brightness thereof is gradually increased. By doing so, the visual target becomes visible to the testee when the visual targets reaches a given brightness. A value corresponding to the brightness when the testee is able to see the visual target is taken as a retinal sensitivity at the point where the visual target is presented. The differences in retinal sensitivity within the visual field are investigated quantitatively by performing similar measurements at each point within the visual field, to thereby create a map. There are subjective tests and objective tests in such static perimetry. Both types of test can be performed using the head-mounted display 2 of the present embodiment. Explanation thereof follows.

A subjective test may be performed in the following manner. First, the head-mounted display 2 is mounted to the head of the testee (user). The testee is asked to hold the testee operated section 420. Next, a visual target for a visual field test is displayed at one point on the display area of the display element 240 according to a command from the controller 400. When doing so, the brightness of the visual target is first made dark, and then the brightness of the visual target is gradually increased. By doing so, even if the visual target is at first dark and not visible by the testee, as the visual target reaches a given brightness, the retina of the testee responds to stimulation from the light, such that the visual target becomes visible to the testee. The testee is asked to press the testee operated section 420 when the visual target becomes visible to the testee. An ON signal is transmitted to the controller 400 when the testee presses the testee operated section 420. The controller 400 performs predetermined processing on receipt of the ON signal, and takes a value corresponding to the brightness at the point of the visual target at this time as the retinal sensitivity at this point. The differences in retinal sensitivity within the visual field are subsequently investigated quantitatively by performing similar measurements for each point within the visual field, to thereby create a retinal sensitivity map.

An objective test may be performed in the following manner. First, the head-mounted display 2 is mounted to the head of the testee. In this scenario, the testee is not required to be asked to hold the testee operated section 420. Then a visual target for a visual field test is displayed at one point on the display area of the display element 240 according to a command from the controller 400. The brightness of the visual target is first made dark, and then the brightness of the visual target is gradually increased. By doing so, even if the visual target is at first dark and not visible by the testee, as the visual target reaches a given brightness, the retina of the testee responds to stimulation from the light, such that the visual target becomes visible to the testee.

When this occurs, the size of the testee's pupil 101 (pupil diameter) changes according to the brightness of the visual target. Specifically, the diameter of the testee's pupil 101 constricts. The change in the state of the eyeball 100 occurring at this time is imaged. Imaging of the eyeball 100 is performed by irradiating infrared radiation from the infrared light sources 310 toward the eyeball 100, and by forming an image light thus obtained from the eyeball 100, into an image on the imaging plane of the imaging element 340 through the observation optical system 300. The timing to start imaging of the eyeball 100 may be set, for example, to a timing prior to displaying the visual target on the display area of the display element 240, or to the same time as displaying the visual target. However, the human retina does not have sensitivity to infrared radiation, and so infrared radiation does not impact the change in state of the eyeball 100.

Image data of the eyeball 100 imaged by the imaging element 340 is acquired by the controller 400. In a process to gradually increase the brightness of the visual target, the controller 400 determines whether or not there has been a change (constriction) of the testee's pupil diameter in response to the brightness of the visual target based on the image data acquired from the imaging element 340. A value corresponding to the brightness at the point of the visual target at the time when it was determined that the testee's pupil diameter has changed is taken as the sensitivity at that point on the retina. The differences in sensitivity on the retina within the visual field are subsequently investigated quantitatively by automatically performing a series of similar measurements for each point within the visual field, and a retinal sensitivity map is created automatically. Note that an objective test may be performed by a single supra-threshold stimulus method in which a bright visual target is displayed at a point on the display area of the display element 240, and a sensitivity map is created by observing the degree of constriction of the pupil diameter.

4. Fixing Stand Configuration

Figure 6:
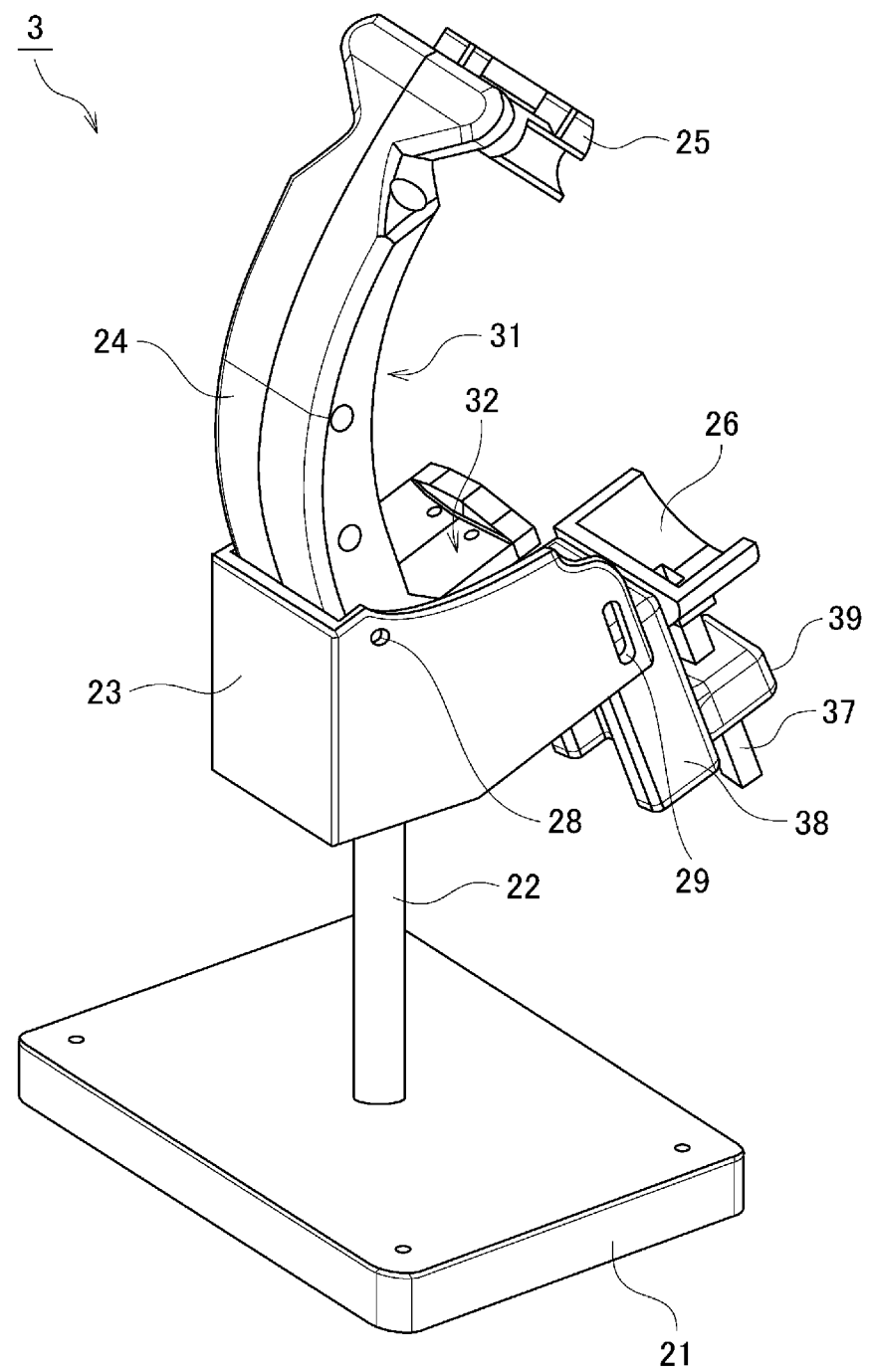
FIG. 6 is a perspective view illustrating an example of a configuration of a fixing stand (head-mounted display fixing stand) according to an embodiment of the present invention.
Figure 7:
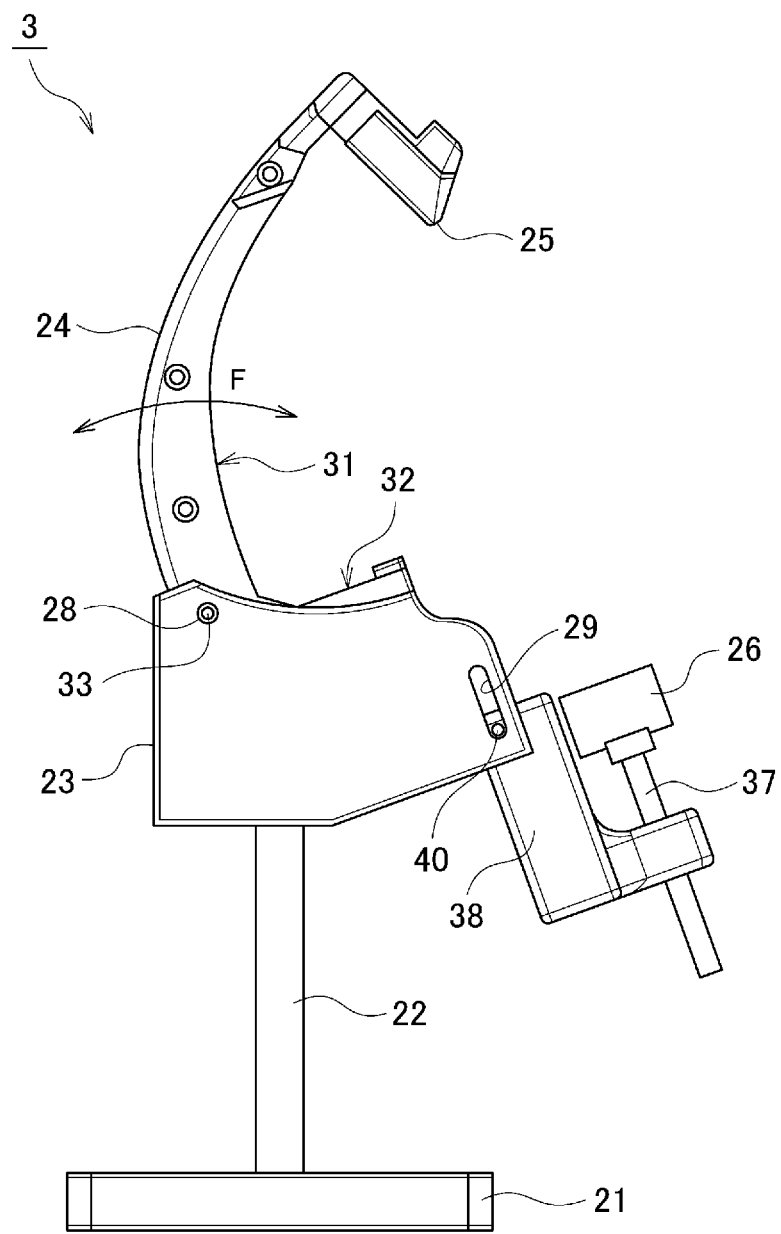
FIG. 7 is a side view illustrating an example of a configuration of a fixing stand (head-mounted display fixing stand) according to an embodiment of the present invention.

FIG. 6 is a perspective view illustrating an example of a configuration of a fixing stand (head-mounted display fixing stand) according to an embodiment of the present invention, and FIG. 7 is a side view of the same.

The illustrated fixing stand 3 has a configuration including a base member 21, a support column 22, a pedestal mount 23, a retaining member 24, a clamping implement 25, and a chin rest 26. The fixing stand 3 is configured so as to be portable, enabling the set up place and orientation of the fixing stand 3 to be changed.

(Base Member)

The base member 21 is a stand to give overall support to the fixing stand 3. The base member 21 can, for example, be configured from a metal material (including alloys) such as stainless steel or brass. The base member 21 is formed in a plate shape with a rectangular profile in plan view. However, the profile of the base member 21 may be a profile other than a rectangle. Moreover, the thickness of the base member 21 may be a uniform constant thickness, or may be thickness with local differences.

(Support Column)

The support column 22 may be configured, for example, similarly to the base member 21 described above, from a metal material (including alloys) such as stainless steel or brass. The support column 22 is installed in a vertically upright state at a center portion of the base member 21. The support column 22 is fixed to the base member 21 using non-illustrated screws, or the like.

(Pedestal Mount)

Figure 8:
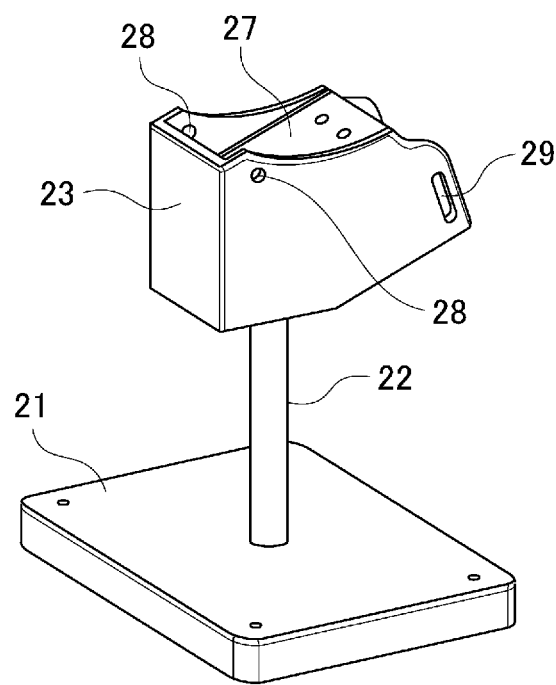
FIG. 8 is a perspective view illustrating an assembled state of a base member, support column, and pedestal mount.

The pedestal mount 23 may be formed, for example, from a resin material. The pedestal mount 23 is arranged at an upper end of the support column 22. The pedestal mount 23 is fixed to the support column 22 using non-illustrated screws, or the like. The base member 21, the support column 22, and the pedestal mount 23 are thereby assembled into a single unit, as illustrated in FIG. 8. A "support mechanism" of the present invention is configured by the base member 21, the support column 22, and the pedestal mount 23 as illustrated in FIG. 8. The support mechanism supports the retaining member 24.

A seating face 27 is provided on the pedestal mount 23. The seating face 27 bears and supports a lower portion of the retaining member 24. The seating face 27 is formed in a substantially letter L-shape in side view. Moreover, first fixing holes 28 to fix the retaining member 24 to the pedestal mount 23, and second fixing holes 29 to fix the chin rest 26 to the pedestal mount 23, are formed in the pedestal mount 23. The first fixing holes 28 thereof are round holes, and the second fixing holes 29 thereof are elongated holes. The reason the second fixing holes 29 made as elongated holes is to make the position of the chin rest 26 adjustable.

(Retaining Member)

Figure 9:
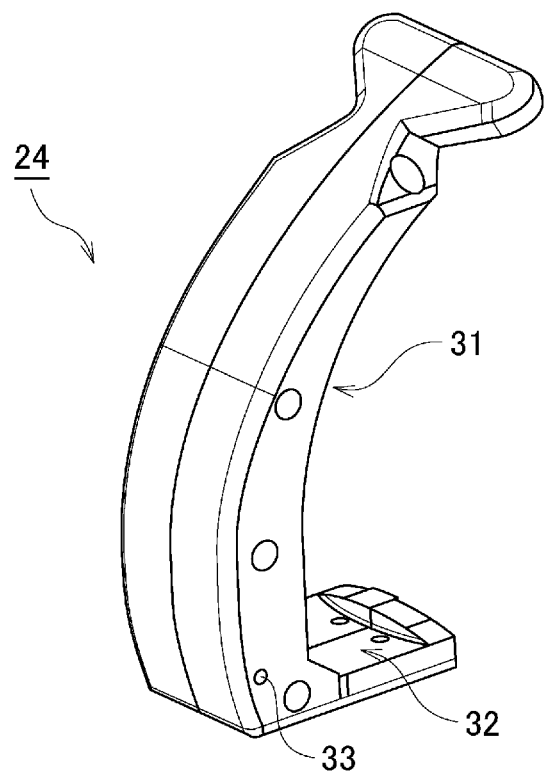
FIG. 9 is a perspective view illustrating a configuration of a retaining member.

The retaining member 24 retains the head-mounted display 2 in a fixed state. The head-mounted display 2 is detachably mounted to the retaining member 24. The retaining member 24 may be configured, for example, from a resin material, similarly to the pedestal mount 23 described above. The retaining member 24 is formed with a substantially bow-shaped profile in side view, so as to run along the outer face profile of the front portion 7 of the head-mounted display 2. As illustrated in FIG. 9, a first bearing section 31 and a second bearing section 32 are formed on the retaining member 24. The first bearing section 31 and the second bearing section 32 are formed at the inner face side of the retaining member 24. The first bearing section 31 is used to bear and support the outer face of the front portion 7 of the head-mounted display 2 from the front. The first bearing section 31 is curved to follow the outer face profile of the front portion 7, such that there is a close contact state when the outer face of the front portion 7 of the head-mounted display 2 is borne and supported by the first bearing section 31. The second bearing section 32 bears and supports the lowest portion of the front portion 7 of the head-mounted display 2 from below. The second bearing section 32 is formed as a single body with the retaining member 24, in a state bending toward the rear from the lower end portion of the first bearing section 31 at substantially a right angle.

Screw holes 33 are formed in a lower end portion of the retaining member 24. The screw holes 33 are provided to the retaining member 24 in order to detachably attach the retaining member 24 to the pedestal mount 23. The screw holes 33 are provided at positions to align with the first fixing holes 28 of the pedestal mount 23. The screw holes 33 are arranged such that the first fixing holes 28 and the screw holes 33 are substantially coaxial when the lower portion of the retaining member 24 is placed on the seating face 27 of the pedestal mount 23.

In reality, fastening knobs, not illustrated in the drawings, are used to attach the retaining member 24 to the pedestal mount 23. These fastening knobs include integral male threads. The male threads of the fastening knobs pass through the first fixing holes 28 of the pedestal mount 23 and screw into the screw holes 33 of the retaining member 24. The retaining member 24 can be fastened and fixed to the pedestal mount 23 by rotating the fastening knobs in one direction in this screwed-in state. Moreover, the retaining member 24 can be swung in the direction F of FIG. 7, with the male threads of the fastening knobs as a center, in a state in which fastening by the fastening knobs has been loosened. The swing action of the retaining member 24 is an action to make the front-rear tilting angle of the head-mounted display 2 mounted to the retaining member 24 adjustable. Two female threads (not illustrated in the drawings) are formed with left-right symmetry in an upper portion of the retaining member 24. These female threads are for attaching the clamping implement 25 to the retaining member 24 by screw fastening.

(Clamping Implement)

Figure 10:
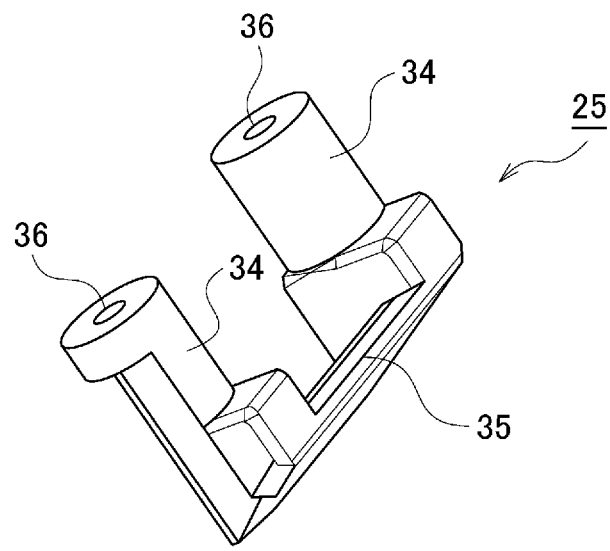
FIG. 10 is a perspective view illustrating a configuration of a clamping implement.
Figure 11:
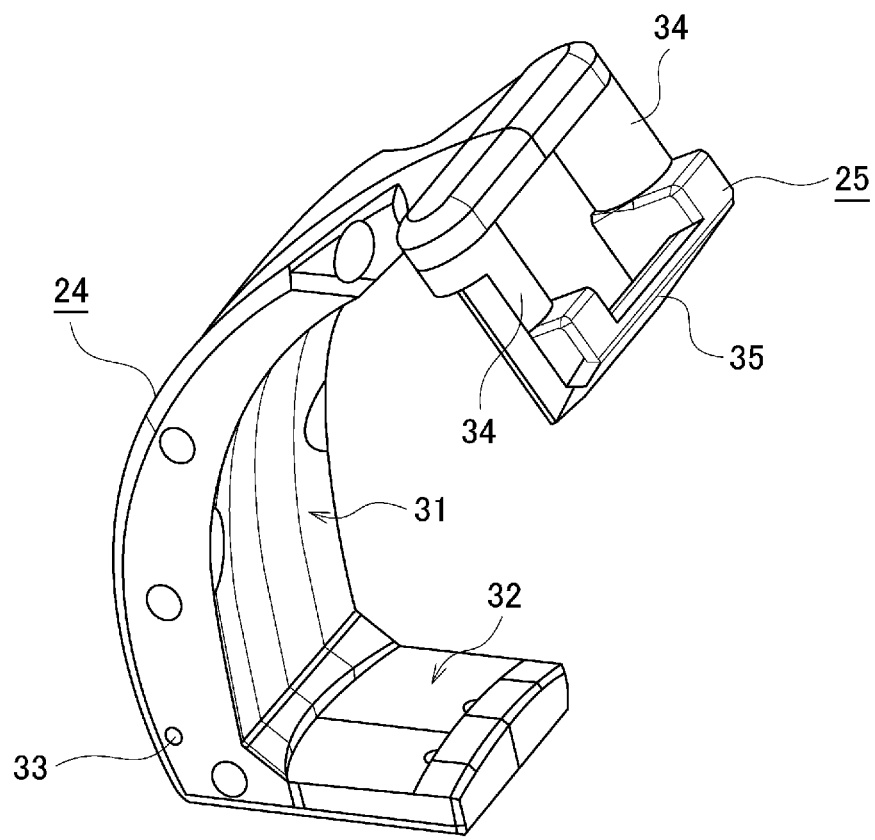
FIG. 11 is a perspective view illustrating a clamping implement in an assembled state to a retaining member.

The clamping implement 25 is for fixing the head-mounted display 2 to the retaining member 24, and clamps a portion of the head-mounted display 2. The clamping implement 25 may be configured, for example, from a resin material, similarly to the retaining member 24 described above. As illustrated in FIG. 10, the clamping implement 25 is a single body including two legs 34 and a coupling section 35 coupling the two legs 34 together. An axial hole 36 is formed in each of the two legs 34. These axial holes 36 are aligned in position with the female threads of the retaining member 24 when the clamping implement 25 is attached to the retaining member 24. In such a state, the clamping implement 25 can be fixed to the retaining member 24 as illustrated in FIG. 11 by passing non-illustrated fixing screws through the axial holes 36 and screwing the fixing screws into the female threads of the retaining member 24.

(Chin Rest)

Figure 12:
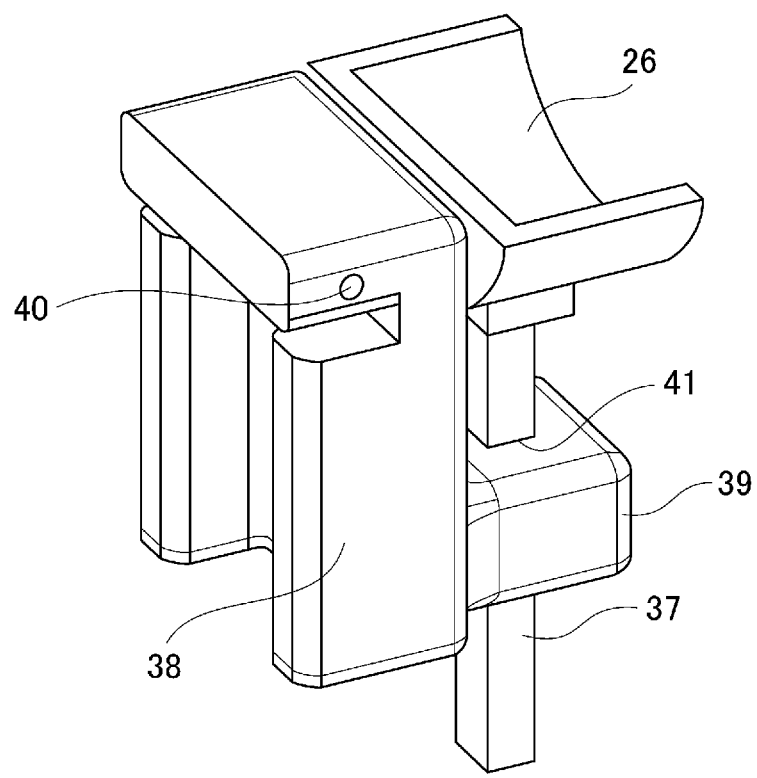
FIG. 12 is a perspective view to explain a configuration of a chin rest.

The chin rest 26 is used for bearing and supporting the chin of a user from below. A concave surface profile is formed to an upper section of the chin rest 26 so as to conform to the profile of a human chin. The chin rest 26 is supported by a support shaft 37, as illustrated in FIG. 12. The chin rest 26 is configured, for example, from a resin material, and is fixed to an upper end of the support shaft 37. The support shaft 37 supporting the chin rest 26 is formed in a bar shape having a rectangular cross-section. A bracket 38 is attached to the support shaft 37. A projection 39 and two screw holes 40 (only one of which is illustrated in FIG. 12) are provided to the bracket 38. A rectangular profile through hole 41 corresponding to the cross-section profile of the support shaft 37 is provided in the projection 39, and the support shaft 37 fits into the through hole 41. In a state in which the support shaft 37 is fitted into the through hole 41, an appropriate amount of sliding resistance acts on the fitted portions of the two members, such that the support shaft 37 is able to move against this sliding resistance in the central axis direction of the through hole 41. Moreover, the position of the chin rest 26 is adjustable by moving the support shaft 37.

The screw holes 40 are formed in order to attach the bracket 38 to the pedestal mount 23. When the bracket 38 is actually attached to the pedestal mount 23, the screw holes 40 are aligned in position with the second fixing holes 29 of the pedestal mount 23, and, in this state, non-illustrated screws are passed through the second fixing holes 29 and screwed into the screw holes 40. These screws are then fastened with an appropriate force. The bracket 38 can thereby be fixed to the pedestal mount 23 (see FIG. 6 and FIG. 7). Moreover, the bracket 38 can be moved in the length direction of the second fixing holes 29 by loosening the screws passing through the second fixing holes 29.

5. Usage Procedure of Head-Mounted Display Unit

Next, explanation follows regarding a usage procedure of the head-mounted display unit.

The head-mounted display unit 1 according to an embodiment of the present invention enables a head-mounted display 2 originally used in a mobile mode to also be used in a fixed mode. Accordingly, hereafter follows an explanation of a procedure to employ the head-mounted display 2 in the fixed mode. This usage procedure includes a first stage in which the head-mounted display 2 is mounted to the fixing stand 3, and a second stage in which the head-mounted display 2 is mounted to the head of the user. Explanation follows regarding a specific procedure for each stage.

(First Stage)

The head-mounted display 2 is first mounted to the fixing stand 3. When doing so, the harness 6 on the head-mounted display 2 is removed from the body section 5 and placed to one side. Moreover, the clamping implement 25 on the fixing stand 3 is removed from the retaining member 24 and placed to one side. In this state, the body section 5 of the head-mounted display 2 is then placed on the retaining member 24 of the fixing stand 3. When this is performed, the front portion 7 of the body section 5 is pressed against the first bearing section 31 and the second bearing section 32 of the retaining member 24.

The clamping implement 25 is then attached to the retaining member 24. When doing so, the two legs 34 of the clamping implement 25 are each arranged at the two respective sides of the intermediate portion 8 of the body section 5. This results in a state in which the two legs 34 straddle the intermediate portion 8 of the body section 5. In this state, the fixing screws are passed through the axial holes 36 of the clamping implement 25, and these screws are screwed into the female threads on the retaining member 24 side and fastened up by an appropriate amount. When this is done, the intermediate portion 8 of the body section 5 is pressed against the retaining member 24 side by the coupling section 35 of the clamping implement 25. The intermediate portion 8 of the body section 5 is thereby in a clamped state, clamped by the clamping implement 25.

The head-mounted display 2 is mounted to the fixing stand 3 by the above procedure. The head-mounted display 2 is thereby retained in a fixed state by the retaining member 24 of the fixing stand 3. The "fixed state" referred to here means a state in which the head-mounted display 2 is fixed at least to such an extent that there are no problems in practice when the head-mounted display 2 is used and mounted to the fixing stand 3. When the head-mounted display 2 is actually used, the forehead of the user lightly presses against the pad as the head-mounted display 2 is put on the head of the user to look through the left and right observation windows. At this point in time, the pressing force imparted to the head-mounted display 2 through the pad is borne by the retaining member 24, and there are no problems in practice as long as the head-mounted display 2 is retained so as not to move. With regards to this point, due to a configuration being adopted in the present embodiment in which the outer face of the front portion 7 is placed in close contact with the first bearing section 31 of the retaining member 24 to retain the head-mounted display 2, the pressing force when the forehead of user is pressed against the pad can be borne in a balanced manner by the whole of the retaining member 24.

Moreover, when the head-mounted display 2 is mounted to the fixing stand 3 in this manner, the head-mounted display 2 is supported in a forward-tilting orientation. The forward-tilting orientation refers to a state in which the optical axis 280a of the optical system illustrated in FIG. 5 is disposed so as to tilt diagonally downward and forward when viewed from the eyeball position. When the tilting angle of the optical axis is defined as being the forward-tilting angle of the head-mounted display 2, the condition for setting the forward-tilting angle is preferably from 5 degrees to 70 degrees, and is more preferably from 15 degrees to 60 degrees, and is still more preferably from 25 degrees to 50 degrees. When the head-mounted display 2 supported in the forward-tilting orientation is mounted to the head of the user, the head-mounted display 2 is in the forward-tilting orientation, and the head of the user is also in a forward-tilting state. Thus, when the user is looking straight ahead at the front face so as to look through the left and right observation windows in the head-mounted display 2, the gaze of the user also tilts diagonally downward and forward.

Moreover, if the retaining member 24 is placed on the seating face 27 of the pedestal mount 23 with the fastening knobs fixing the retaining member 24 to the pedestal mount 23 in a loosened state, then the retaining member 24 can be swung in the direction F of FIG. 7. This enables to adjust the front-rear direction tilt angle (the forward-tilting angle in the present embodiment) of the head-mounted display 2 mounted to the retaining member 24.

Second Stage

Next, the head-mounted display 2 is mounted to the head of the user. When doing so, the fixing stand 3 mounted with the head-mounted display 2 may be set up on a table. The user may, moreover, sit on a chair so as to be face-to-face with the rear portion 9 of the head-mounted display 2, and then mount the head-mounted display 2 to his/her head. When doing so, the position of the chin rest 26 may be lowered and retracted out of the way in advance so that the chin rest 26 does not get in the way. In this state, the user inserts their own head inside of the body section 5 while aligning to the position of the head-mounted display 2. This results in a state in which the head-mounted display 2 is worn on the head of the user. The user determines the position of their head when doing so by pressing their forehead against the pad of the body section 5 and looking through the left and right observation windows. After thus determining the head position, while maintaining this state, the position of the chin rest 26 is moved upward such that the chin rest 26 abuts the chin of the user. The position of the chin rest 26 after moving may be retained by utilizing the sliding resistance between the support shaft 37 and the through hole 41. Alternatively, the position of the chin rest 26 may be fixed by pressing screws or the like (not illustrated in the drawings) against the support shaft 37 from the side. The movement of the head of the user is thereby restricted by the body section 5 of the head-mounted display 2 and the chin rest 26.

The user then aligns the central positions of the optical systems to the pupil center positions by appropriately rotating the first rotatable knobs 11 and the second rotatable knobs 12 while looking through the two observation windows of the head-mounted display 2, and matches the distances from the positions of the pupils to respective front lens positions of the optical systems. When doing so, an image for use in positioning may be displayed on the display element 240 described above, such that a user is able to appropriately rotate the first rotatable knobs 11 and the second rotatable knobs 12 while looking at this image. Moreover, image data of the eyeball 100 imaged by the imaging element 340 may be transmitted to an external terminal device, so that a tester (someone other than the user) can appropriately rotate the first rotatable knobs 11 and the second rotatable knobs 12 while viewing the image data on the screen of this terminal device, or so that the tester can instruct the user on how to make adjustments.

The preparation for using the head-mounted display 2 as a fixed type display is completed by performing the above. This enables a visual field test to be performed with the head-mounted display 2 remaining fixed to the fixing stand 3. Note that in order to return the usage mode of the head-mounted display 2 from fixed type to mobile type, the body section 5 together with the clamping implement 25 may be detached from the retaining member 24, and then the harness 6 may be attached to the body section 5.

6. Advantageous Effects of Embodiment

In the embodiment of the present invention, mounting the head-mounted display 2 to the fixing stand 3 enables the head-mounted display 2 to be used in a fixed state (as a fixed type) at a particular location. The weight of the head-mounted display 2 is accordingly supported by the fixing stand 3, such that the weight of the head-mounted display 2 is no longer added on the user mounted with the head-mounted display 2 on his/hear head. This enables physical burden on the user to be reduced. As a result, users of a wide range of ages from children to elderly persons are able to use the head-mounted display 2 while feeling substantially no burden. Thus when, for example, the head-mounted display 2 is employed as an eye testing device such as a visual field testing device, an eye test can be performed without burden to the testee even if the testee is a child or an elderly person. Moreover, due to the head-mounted display 2 being attachable to and detachable from the fixing stand 3, the head-mounted display 2 can be used in both mobile and fixed modes.

Moreover, although there are glasses type, goggle type, and helmet type head-mounted displays and the like for the head-mounted display, the present invention is particularly preferably applicable when using the helmet type or similar style. The reasons for this are given below.

The glasses type head-mounted displays are made so as to be extremely light, and a user feels no burden on the neck or the like caused by the weight of the head-mounted display during use. In contrast thereto, the helmet type head-mounted displays tend to be heavier than the glasses type head-mounted displays. The head-mounted display 2 in the present embodiment is a helmet style head-mounted display, and has a weight of about 1.8 kg due to the optical systems (200, 300) as illustrated in FIG. 5 above, the controller 400, and the like being installed in the body section 5. This means that a burden is liable to be felt on the neck, shoulders, etc. of a user during use. In such cases, physical burden on the user can be greatly reduced by using the fixing stand 3 to employ the head-mounted display 2 as the fixed type head-mounted display. However, the present invention is not limited to the helmet type head-mounted display, and may be configured using the goggle type head-mounted display. Although the weight of goggle type head-mounted displays varies according to the components installed therein, the user will feel a burden if the weight is greater than a given weight. Similar advantageous effects are accordingly expected in applications to the goggle type head-mounted displays.

In the embodiment of the present invention, when the head-mounted display 2 is mounted to the fixing stand 3, the fixing stand 3 supports the head-mounted display 2 in a forward-tilting orientation, and so the user using the head-mounted display 2 is able to place their forehead against the pad at the inside of the front portion 7 so that the weight of the head is supported. Thus, the user is able to use the head-mounted display 2 in an orientation of adding less burden.

In the embodiment of the present invention, due to the fixing stand 3 being configured so as to be portable, the place of use can be freely selected and changed even when using the head-mounted display 2 as a fixed type display.

In the embodiment of the present invention, due to the front-rear tilting angle of the head-mounted display 2 being adjustable, the user using the head-mounted display 2 is able to make the tilting angle of the head-mounted display 2 match the orientation of the user such that the user feels relaxed when using the head-mounted display 2. Moreover, the tilting angle of the head-mounted display 2 can be matched so that the head-mounted display 2 is easily mounted to the head of the user. This enables the in-use feeling of the head-mounted display 2 to be improved.

In the embodiment of the present invention, the chin rest 26 is provided to the fixing stand 3 in a configuration in which the chin of the user is supported by the chin rest 26. The position of the head of the user mounted with the head-mounted display 2 can accordingly be stabilized.

In the embodiment of the present invention, due to a mechanism to adjust the position of the chin rest 26 (in particular, the position in the height direction) being provided to the fixing stand 3, the chin rest 26 can be moved to an appropriate position to match the size of the head of the user using the head-mounted display 2.

7. Other Embodiments

Figures 13A, 13B:
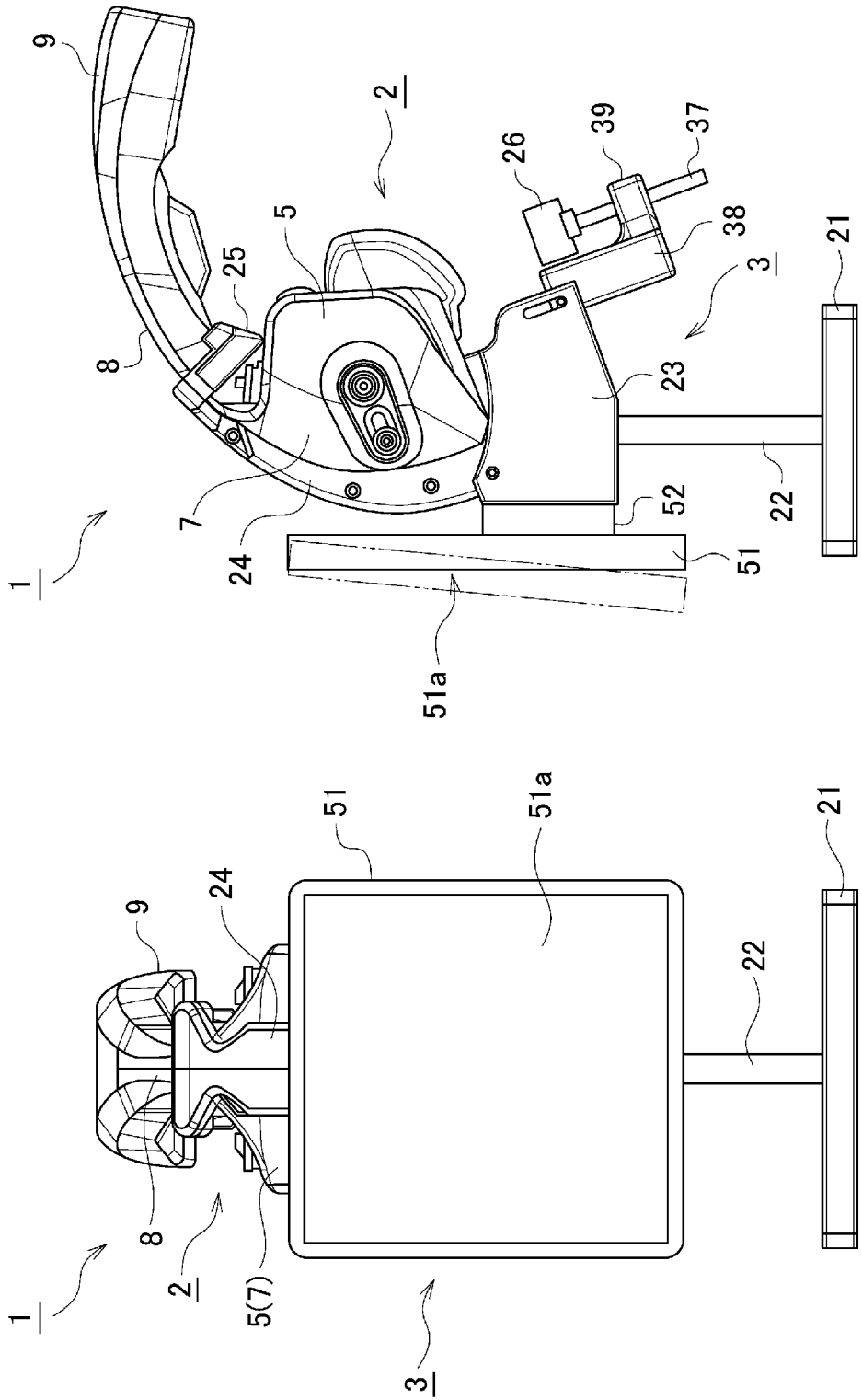
FIG. 13A is a front view thereof and FIG. 13B is a side view thereof.

FIG. 13 illustrates a configuration of a head-mounted display unit according to another embodiment of the present invention, FIG. 13A being a front view thereof, and FIG. 13B being a side view thereof.

In this embodiment a monitor 51 is provided to the fixing stand 3. The monitor 51 displays images to someone other than the user using the head-mounted display 2. The monitor 51 may be configured by a flat screen liquid crystal display device or organic EL display device, or a tablet terminal or the like may be employed therefor. A support member 52 is fixed to the back face of the monitor 51, and the monitor 51 is attached to the pedestal mount 23 via the support member 52 by using screw fastening or the like.

The monitor 51 includes a display area 51a, and the display area 51a is disposed in a state orientated in front of the retaining member 24. Reference "in front of the retaining member 24" means the Y direction indicated in FIG. 1, and is the direction in which the face of the user is facing when the head-mounted display 2 mounted to the retaining member 24 is mounted to the head of the user for use.

The orientation of the monitor 51 is also adjustable. A mechanism to adjust the orientation of the monitor 51 may employ, for example, a hinge mechanism or the like. Thereby, for example, as indicated by the double-dot broken line in the drawing, the orientation of the monitor 51 can be adjusted. Moreover, a mechanism to adjust the orientation of the monitor 51 preferably employs a configuration such that the display area 51a can be orientated in all directions around a given axis. Specifically, the following configuration may be employed therefor. First, so as not to have a detrimental effect on the stability of the fixing stand 3, the base member 21 is set to a larger size and a pole (not illustrated in the drawings) that is sufficiently long in the vertical direction is set upright on the base member 21. Then a clasp (not illustrated in the drawings) is attached to the pole, the clasp being rotatable around a central axis (vertical axis) of the pole. Then, the monitor 51 is mounted to the clasp at a height position such that the monitor 51 does not impinge on the retaining member 24, the head-mounted display 2, or the like when changing the orientation of the monitor 51. Employing such a configuration enables the monitor 51 (the display area 51a) to be orientated in all directions around the vertical axis by rotating the clasp. Moreover, if the pole described above is made in the shape of an entrance arch (inverted letter U-shaped) or H-shape, and a clasp is rotatably attached to a horizontal portion of the pole in a similar manner to as described above, the monitor 51 (the display area 51a) can then be moved in all directions around a horizontal axis by rotating the clasp.

In this embodiment, due to the monitor 51 being provided to the fixing stand 3, for example, the same images to the images seen by the user using the head-mounted display 2 can be displayed on the monitor 51. This enables someone other than the user to look at the monitor 51 and confirm what sort of image the user is looking at when using the head-mounted display 2. Moreover, when the head-mounted display 2 is employed as an eye testing device, a tester who is seated in front of the testee whose head is mounted with the head-mounted display 2 can check the display area 51a of the monitor 51. The tester is thereby able to give instructions to the testee while necessary information for an eye test is being displayed on the monitor 51. Moreover, by displaying an image of an eyeball imaged by the imaging element 340 on the monitor 51, the tester is able to perform adjustment operations using the first rotatable knobs 11 and the second rotatable knobs 12 while looking at the eyeball image.

Moreover, due to adopting a configuration in which the orientation of the monitor 51 can be adjusted, the orientation of the monitor 51 can be aligned so as to be easily seen by someone other than the user.

Note that the monitor 51 may be disposed in a state in which the display area 51a is orientated at the side of the retaining member 24 (one of the X directions). Such cases enable the tester seated at the side of the testee whose head is mounted with the head-mounted display 2 to check the display area 51a of the monitor 51.

Moreover, a configuration may be employed in which the orientation of the monitor 51 can be changed to at least two different directions from out of: a forward facing state of the display area 51a; a rearward facing state of the display area 51a, a left facing state of the display area 51a; a right facing state of the display area 51a; an upward facing state of the display area 51a; and a downward facing state of the display area 51a. This enables the orientation of the monitor 51 to be switched according to the set up place of the head-mounted display unit 1 and the fixing stand 3.

Figure 14:
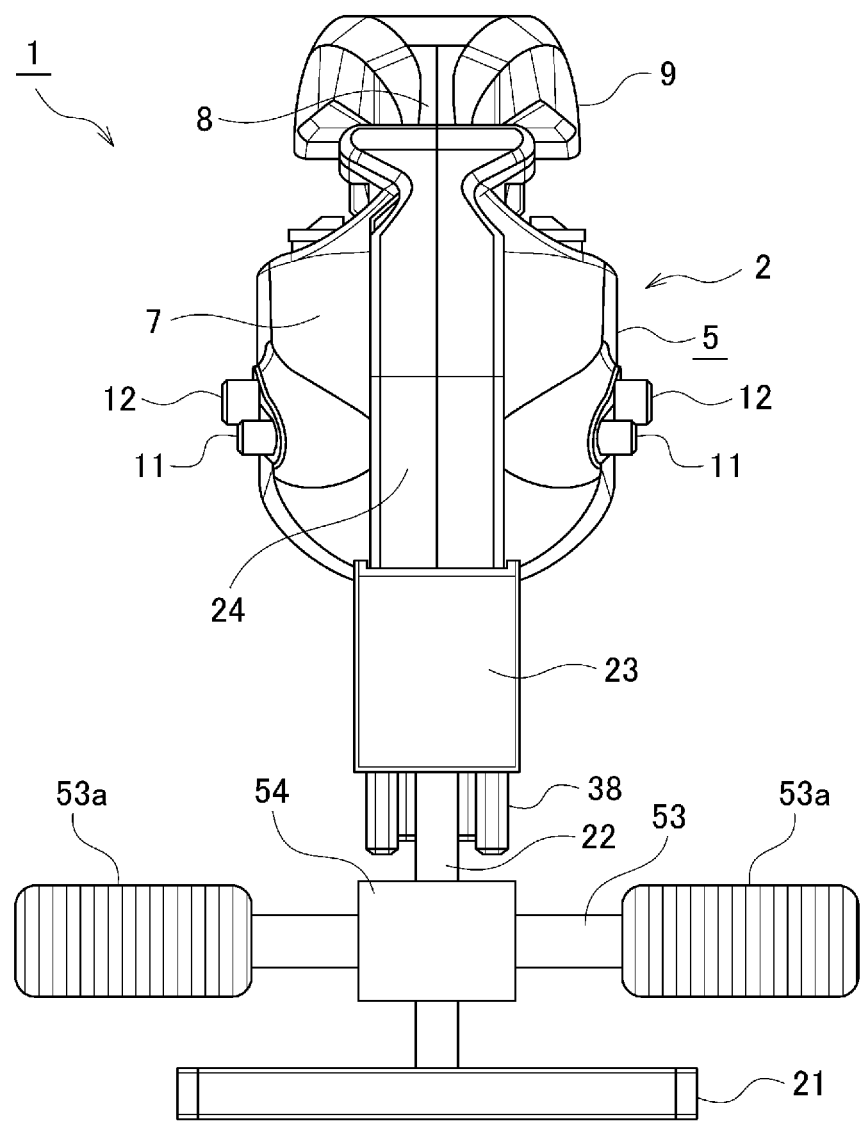
FIG. 14 is a front view illustrating a configuration of a head-mounted display unit according to yet another embodiment of the present invention.

FIG. 14 is a front view illustrating a configuration of a head-mounted display unit according to yet another embodiment of the present invention.

A handle 53 is provided to the fixing stand 3 in this embodiment. The handle 53 is disposed at a lower position than the retaining member 24. Moreover, the handle 53 is fixed to a support column 22 using a coupling member 54.

A left and right pair of grips 53a are provided to the handle 53. The grips 53a are disposed at the two respective ends of the handle 53. The grips 53a are portions gripped by the two hands of a user when the user is using the head-mounted display 2 mounted to the fixing stand 3. The grips 53a are formed with a thickness easily gripped by the user. Moreover, anti-slip processing may be performed on the grips 53a as required. Specifically, the surface of the grips 53a may be configured with a high friction material such as rubber, or the surface of the grips 53a may be processed to provide indentations and protrusions thereon.

In the present embodiment, when using the head-mounted display 2 mounted to the retaining member 24 by mounting to the head of the user, the orientation of the user can be stabilized by the user gripping the left and right grips 53a with both hands. Moreover, the overall orientation of the head-mounted display unit 1 can be stabilized by the hands of a user adding downward force to the base member 21.

Note that a configuration may be adopted in which the position of the handle 53 is adjustable in the up-down direction or in the front-rear direction. Moreover, a vertical orientation may be adopted for the grips 53a by bending the two ends of the handle 53 upward. Moreover, by configuring the testee operated section 420 operated by the testee in a visual field test or the like by, for example, a press switch, and by providing such a testee operated section 420 on at least one of the left or right grips 53a, a configuration is achieved in which the testee operated section 420 is operable (operable by switching) while the testee is still gripping the grips 53a.

Moreover, in addition to the embodiments described above, for example, although not illustrated in the drawings, a configuration may be adopted in which a terminal section is provided to each of the head-mounted display 2 and the fixing stand 3. Specifically, a first terminal section (for example, a male terminal) may be provided to the head-mounted display 2, and a second terminal section (for example, a female terminal) may be provided to the retaining member 24, so as to adopt a configuration in which the first terminal section and the second terminal section are electrically connected together when the head-mounted display 2 has been mounted to the retaining member 24.

When a configuration such as that described above is adopted, for example, if a rechargeable battery is installed in the head-mounted display 2, then the first terminal section and the second terminal section can function as terminal sections to charge the rechargeable battery. In such cases, the first terminal section is a terminal section for receiving power, and the second terminal section is a terminal section for supplying power. This enables charging to start automatically simply by mounting the head-mounted display 2 to the fixing stand 3, and for the mounted time to be used in full as charging time. Moreover, when the head-mounted display 2 is employed in an eye test, the time required for the eye test can be used for charging.

However, other than being utilized as terminal sections for charging, the first terminal section and the second terminal section may, for example, be utilized to input a signal to the controller (computer) 400 of the head-mounted display 2 or to output a signal from the controller 400. Moreover, using the second terminal section as an input terminal to the monitor 51 enables images of the eyeball that have been imaged by the imaging element 340 and processed by the controller 400 to be displayed on the monitor 51.

9. Modified Examples Etc

The technical scope of the present invention is not limited to the embodiment described above but includes various modes and modifications as far as the specific effects obtained by the constituent features of the invention and combinations thereof can be derived.

For example, although the pedestal mount 23 is fixed to the support column 22 in the embodiments above, there is no limitation thereto. A configuration may be adopted in which the position of the pedestal mount 23 is adjustable with respect to the axial direction (up-down direction) of the support column 22. Adopting such a configuration enables the height of the pedestal mount 23 to be adjusted to match the height of the user and the seat height.

Moreover, although the harness 6 is removed from the body section 5 when mounting the head-mounted display 2 on the fixing stand 3 for use in the embodiments above, there is no limitation thereto. A mechanism to shift the harness 6 to a position out of the way of the user and to keep the harness 6 in such a position may be provided to the body section 5. Specifically, for example, a mechanism may be provided in which a hook portion (not illustrated in the drawings) is provided to the rear portion 9 of the body section 5, and the harness 6 is hooked onto and retained on the hook portion.

Moreover, although the head-mounted display 2 is supported by the fixing stand 3 in a forward-tilting orientation in the embodiments described above, there is no limitation thereto. A configuration may be adopted in which the head-mounted display 2 is supported in a horizontal orientation or in an orientation tilted rearward. However, supporting the head-mounted display 2 in a forward-tilting orientation has the advantage of reducing the burden on the user.

Moreover, although the chin rest 26 is provided to the fixing stand 3 in the embodiments described above, it is sufficient to provide the chin rest 26 only when required. Moreover, in cases in which the chin rest 26 is provided, a configuration may be adopted in which the relative positions of the retaining member 24 and the chin rest 26 are adjustable in the left-right direction and/or the front-rear direction.

Moreover, although an example has been explained in which the fixing stand 3 is set up for use on a table in the embodiments described above, there is no limitation thereto. For example, a fixing stand set up for use by installing on the ceiling, wall, or the like of a building using screw fastenings etc. may be employed. Moreover, for the fixing stand 3 set up for use on a table, in order to stabilize the set up state of the fixing stand 3, a configuration may be adopted in which a clamping mechanism (not illustrated in the drawings) is provided to the base member 21, to enable the base member 21 to be fixed to the table using the clamping mechanism. Moreover, an adhesive sheet (not illustrated in the drawings) may be adhered to a bottom face of the base member 21 so that the fixing stand 3 does not move on the table.

There is no particular limitation to the weight of the head-mounted display 2 to which the present invention is applicable. However, in consideration of the perspective of reducing physical burden on the user, the present invention is preferably applied to cases in which a head-mounted display 2 with a weight of 500 g or greater is employed, and is particularly applied to cases in which a head-mounted display 2 with a weight of 1 kg or greater is employed.

Moreover, the present invention may be applied to cases in which the head-mounted display is employed for a medical application other than eye testing, or moreover applied to cases other than medical applications (for example, gaming machines, AV equipment, or the like).

Furthermore, the present invention is not only applicable to cases in which the head-mounted display 2 mounted to the fixing stand 3 is used while a user is seated on a chair, and may also be applied to cases in which the user remains standing for use, or the user is lying back on a seat with a backrest or a sofa.

EXPLANATION OF THE REFERENCE NUMERALS 1 head-mounted display unit
2 head-mounted display
3 fixing stand
5 body section
6 harness
21 base member
22 support column 23 pedestal mount
24 retaining member
25 clamp
26 chin rest
51 monitor
51a display area
53 handle
53a grip

The invention claimed is:

1. A head-mounted display unit comprising:
   a head-mounted display comprising a body section having a display element for displaying images and a harness for mounting the body section to a head of a user; and
   a fixing stand comprising a retaining member configured so as to enable the attachment and detachment of the front portion of the body section, and so as to enable the body section to be retained in a fixed state and a support mechanism configured so as to support the retaining member.

2. The head-mounted display unit of claim 1, wherein the retaining member retains the body section in a forward-tilting orientation.

3. The head-mounted display unit of claim 1, wherein the fixing stand is portable.

4. The head-mounted display unit of claim 1, wherein the head-mounted display is a head-mounted type eye testing device.

5. A head-mounted display fixing stand for fixing a head-mounted display comprising a body section having a display element for displaying images and a harness for mounting the body section to a head of a user for use, the head-mounted display fixing stand comprising:
   a retaining member configured so as to enable the detachable mounting of the front portion of the body section and so as to retain the mounted body section in a fixed state; and
   a support mechanism to support the retaining member.

6. The head-mounted display fixing stand of claim 5, wherein a retaining member configured so as to retain the body section so that a tilting angle of the body section is adjustable in a front-rear direction.

7. The head-mounted display fixing stand of claim 5, further comprising a chin rest to support the chin of a user using the head-mounted display.

8. The head-mounted display fixing stand of claim 7, wherein the position of the chin rest is adjustable.

9. The head-mounted display fixing stand of claim 5, further comprising a monitor to display images to someone other than a user using the head-mounted display.

10. The head-mounted display fixing stand of claim 9, wherein the monitor is disposed in a state in which a display area of the monitor is orientated in front of or at a side of the retaining member.

11. The head-mounted display fixing stand of claim 9, wherein an orientation of the monitor is adjustable.

12. The head-mounted display fixing stand of claim 5, further comprising a handle including a left and right pair of grips.

13. The head-mounted display fixing stand of claim 5, wherein:
   the retaining member includes a second terminal section corresponding to a first terminal section provided to the head-mounted display; and
   the first terminal section and the second terminal section are electrically connected when the head-mounted display is mounted to the retaining member.

14. The head-mounted display fixing stand of claim 13, wherein the first terminal section and the second terminal section are terminal sections for charging a rechargeable battery installed in the head-mounted display.

* * * * *